US009663816B2

(12) United States Patent
Kuwata et al.

(10) Patent No.: US 9,663,816 B2
(45) Date of Patent: May 30, 2017

(54) METHOD FOR MEASURING A COMPONENT OF A BIOLOGICAL FLUID AND REDUCING THE EFFECT OF INTERFERING SUBSTANCES

(71) Applicant: KYOWA MEDEX CO., LTD., Chuo-ku, Tokyo (JP)

(72) Inventors: Hideyuki Kuwata, Sunto-gun (JP); Tomoko Aratake, Sunto-gun (JP); Kenta Kinjo, Sunto-gun (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 0 days.

(21) Appl. No.: 14/391,885

(22) PCT Filed: Apr. 18, 2013

(86) PCT No.: PCT/JP2013/061530
§ 371 (c)(1),
(2) Date: Oct. 10, 2014

(87) PCT Pub. No.: WO2013/161677
PCT Pub. Date: Oct. 31, 2013

(65) Prior Publication Data
US 2015/0079620 A1 Mar. 19, 2015

(30) Foreign Application Priority Data

Apr. 27, 2012 (JP) .................... 2012-103258
May 25, 2012 (JP) .................... 2012-119584

(51) Int. Cl.
*C12Q 1/28* (2006.01)
*G01N 33/92* (2006.01)
*G01N 33/58* (2006.01)
*C09B 21/00* (2006.01)

(52) U.S. Cl.
CPC ............... *C12Q 1/28* (2013.01); *C09B 21/00* (2013.01); *G01N 33/581* (2013.01); *G01N 33/92* (2013.01)

(58) Field of Classification Search
CPC ................. C12Q 1/28; G01N 33/92
USPC ......................................... 435/28
See application file for complete search history.

(56) References Cited

U.S. PATENT DOCUMENTS 3,886,045 A 5/1975 Meiattini
4,491,631 A * 1/1985 Imamura .............. C12N 9/001
435/11
4,554,249 A * 11/1985 Kosaka .................. C12Q 1/26
435/10
5,925,534 A * 7/1999 Miki ..................... C12Q 1/32
435/11
2011/0306072 A1 12/2011 Nicholls et al.

FOREIGN PATENT DOCUMENTS

| JP | 57-071398 | 5/1982 |
| JP | S58-041357 | 10/1983 |
| JP | 60-228963 | 11/1985 |
| JP | 03-010696 | 1/1991 |
| JP | 03-228699 | 10/1991 |
| JP | 07-039394 | 2/1995 |
| JP | 07-155196 | 6/1995 |
| JP | 09-224697 | 9/1997 |
| JP | 11-103888 | 4/1999 |
| JP | 11-243993 | 9/1999 |
| JP | 2004-037431 | 2/2004 |
| JP | 2005-034132 | 2/2005 |
| JP | 2006-081471 | 3/2006 |
| JP | 2011-528122 | 11/2011 |
| WO | 02/086230 | 10/2002 |
| WO | 2008-087896 | 7/2008 |

OTHER PUBLICATIONS

Droge et al. The Fatty Acid Induced Conformational States of Human Serum Albumin Investigated by Means of Multiple Co-Binding of Protons and Oleic Acid; Biochemical Journal, vol. 250 (1988) pp. 443-446.*
Kotani et al. Determination of Plasma Free Fatty Acids by High Performance Liquid Chromatography With Electrochemical Detection; Analytical Biochemistry, vol. 284 (2000) pp. 65-69.*
Okabe et al. Enzymatic Determination of Free Fatty Acids in Serum; Clinical Chemistry, vol. 26, No. 11 (1980) pp. 1540-1543.*
Hasegawa et al., "3-Octenoic Acid o Mochiita Kosoho ni yoru Yuri Shibosan Sokuteiho no Kento", The Journal of Clinical Laboratory Instruments and Reagents, vol. 13, No. .4 (1990) 729-33 (Partial English Translation).
Kikuchi et al., "Kosoho ni yoru Yuri Shibosan Sokuteiho no GREINER IID eno Oyo", Japanese Journal of Clinical Laboratory Automation, vol. 9, No. 2 (1984) 550-53 (Partial English Translation).

* cited by examiner

*Primary Examiner* — Scott Long
*Assistant Examiner* — Paul Martin
(74) *Attorney, Agent, or Firm* — Fitzpatrick, Cella, Harper & Scinto

(57) ABSTRACT

Provided is a measuring method of a component to be measured in a specimen while suppressing an influence of bilirubin. A measuring method of a component to be measured, comprising converting the component to be measured in the specimen to hydrogen peroxide through an enzymatic reaction, reacting the formed hydrogen peroxide with an oxidative-coloring chromogen in the presence of a peroxidase, and measuring an absorbance of the colored reaction solution to thereby determine the component to be measured, wherein a fatty acid or a salt thereof coexists. The measuring method of a component to be measured in a specimen according to the present invention is useful in clinical diagnosis.

3 Claims, No Drawings

METHOD FOR MEASURING A COMPONENT OF A BIOLOGICAL FLUID AND REDUCING THE EFFECT OF INTERFERING SUBSTANCES

TITLE OF THE INVENTION

This application is a national phase of PCT/JP2013/061530 filed Apr. 18, 2013, which in turn claims before of Japanese Patent Application Nos. JP 2012-103258 filed Apr. 27, 2012 and JP 2012-119584 filed May 25, 2012.

TECHNICAL FIELD

The present invention relates to a measuring method of a component to be measured in a specimen and to a measuring reagent of a component to be measured in a specimen.

BACKGROUND ART

There is routinely carried out a clinical test which comprises forming hydrogen peroxide by using an oxidase from a component to be measured in a biological specimen such as serum and measuring the hydrogen peroxide formed to thereby determine the component to be measured. Especially, colorimetric analysis is routinely used in the clinical test. In the colorimetric analysis, the formed hydrogen peroxide is reacted with an oxidative-coloring chromogen in the presence of a peroxidase to form a dye, and the absorbance of the colored reaction solution containing the formed dye is measured to thereby determine the component to be measured in the biological specimen.

In this colorimetric analysis based on measuring hydrogen peroxide, the influence of interfering substances such as ascorbic acid and bilirubin contained in biological specimens often becomes a problem. Especially, as to bilirubin, there is a problem that bilirubin influences the reaction of hydrogen peroxide with an oxidative-coloring chromogen in the presence of a peroxidase, and its reduction action gives a negative influence.

Methods known so far to solve this problem include a method of using a ferrocyanide ion (see patent document 1), a method of using an EDTA-iron complex (see patent document 2), a method of using a ferrocyanide ion and albumin (see patent document 3), a method of using a cationic surfactant and/or an amphoteric surfactant (see patent document 4), a method of using an amphoteric surfactant (see patent document 5), a method of using an amphoteric surfactant and a ferrocyanide (see patent document 6), a method of using a polyoxyethylene alkyl ether having an HLB of 13 or more and a ferrocyanide ion (see patent document 7), a method of using an iron complex and a steroid compound (see patent document 8), and a method of using a polyoxyethylene alkylphenyl ether condensate (see patent document 9).

PRIOR ART DOCUMENTS

Patent Documents

Patent Document 1: Japanese unexamined Patent Application Publication No. 49-050991
Patent Document 2: Japanese unexamined Patent Application Publication No. 57-071398
Patent Document 3: Japanese unexamined Patent Application Publication No. 60-228963
Patent Document 4: Japanese unexamined Patent Application Publication No. 3-010696
Patent Document 5: Japanese unexamined Patent Application Publication No. 7-039394
Patent Document 6: Japanese unexamined Patent Application Publication No. 7-155196
Patent Document 7: Japanese unexamined Patent Application Publication No. 11-103888
Patent Document 8: Japanese unexamined Patent Application Publication No. 11-243993
Patent Document 9: Japanese unexamined Patent Application Publication No. 2004-037431

SUMMARY OF THE INVENTION

Problem to be Solved by the Invention

An object of the present invention is to provide a measuring method of a component to be measured in a specimen while suppressing an influence of bilirubin and a measuring reagent of a component to be measured in a specimen while suppressing the influence of bilirubin.

Means to Solve the Problems

The present inventors have found that, as a result of intensive studies to solve the problem, in a measuring method of a component to be measured, comprising converting the component to be measured in a specimen to hydrogen peroxide through an enzymatic reaction, reacting the formed hydrogen peroxide with an oxidative-coloring chromogen in the presence of a peroxidase, and measuring an absorbance of the colored reaction solution to thereby determine the component to be measured, coexistence of a fatty acid or a salt thereof suppresses the influence of bilirubin, thereby completing the present invention. That is, the present invention relates to the following [1] to [6].

[1] A measuring method of a component to be measured, comprising converting the component to be measured in a specimen to hydrogen peroxide through an enzymatic reaction, reacting the formed hydrogen peroxide with an oxidative-coloring chromogen in the presence of a peroxidase, and measuring an absorbance of the colored reaction solution to thereby determine the component to be measured, wherein a fatty acid or a salt thereof coexists.

[2] The measuring method according to [1], wherein the fatty acid is a saturated or unsaturated fatty acid having 8 to 24 carbon atoms.

[3] The measuring method according to [2], wherein the saturated or unsaturated fatty acid having 8 to 24 carbon atoms is a fatty acid selected from the group consisting of octanoic acid, decanoic acid, lauric acid, myristic acid, palmitic acid, stearic acid, oleic acid, linoleic acid, linolenic acid, eicosatrienoic acid, arachidonic acid, icosanoic acid, eicosatetraenoic acid, eicosapentaenoic acid, docosanoic acid, docosahexaenoic acid, tetradocosanoic acid, and tetracosapentaenoic acid.

[4] A measuring reagent of a component to be measured in a specimen comprising a component for converting a component to be measured in the specimen to hydrogen peroxide through an enzymatic reaction, a peroxidase, an oxidative-coloring chromogen, and a fatty acid or a salt thereof.

[5] The measuring reagent according to [4], wherein the fatty acid is a saturated or unsaturated fatty acid having 8 to 24 carbon atoms.

[6] The measuring reagent according to [5], wherein the saturated or unsaturated fatty acid having 8 to 24 carbon atoms is a fatty acid selected from the group consisting of octanoic acid, decanoic acid, lauric acid, myristic acid, palmitic acid, stearic acid, oleic acid, linoleic acid, linolenic acid, eicosatrienoic acid, arachidonic acid, icosanoic acid, eicosatetraenoic acid, eicosapentaenoic acid, docosanoic acid, docosahexaenoic acid, tetradocosanoic acid, and tetracosapentaenoic acid.

Effect of the Invention

The present invention provides a measuring method of a component to be measured in a specimen while suppressing an influence of bilirubin and a measuring reagent of a component to be measured in a specimen while suppressing the influence of bilirubin.

MODE OF CARRYING OUT THE INVENTION

A measuring method of a component to be measured in a specimen of the present invention is a measuring method of a component to be measured in a specimen, comprising converting the component to be measured in the specimen to hydrogen peroxide through an enzymatic reaction, reacting the formed hydrogen peroxide with an oxidative-coloring chromogen in the presence of a peroxidase, and measuring an absorbance of the colored reaction solution to thereby determine the component to be measured, wherein a fatty acid or a salt thereof coexists.

The fatty acid in the present invention is not particularly limited as long as it is a fatty acid which enables the measuring method of the present invention. Examples of the fatty acid include a saturated or unsaturated fatty acid having 8 to 24 carbon atoms, and a saturated or unsaturated fatty acid having 8 to 18 carbon atoms are preferred. Examples of saturated or unsaturated fatty acids having 8 to 24 carbon atoms include octanoic acid, decanoic acid, lauric acid, myristic acid, palmitic acid, stearic acid, oleic acid, linoleic acid, linolenic acid, eicosatrienoic acid, arachidonic acid, icosanoic acid, eicosatetraenoic acid, eicosapentaenoic acid, docosanoic acid, docosahexaenoic acid, tetradocosanoic acid, and tetracosapentaenoic acid. In addition, the fatty acid of the present invention may be a salt, and examples of the salt include a lithium salt, a sodium salt, a potassium salt, an ammonium salt, a calcium salt, and a magnesium salt. The fatty acid can also be used in combinations of two or more in the present invention. The concentration of the fatty acid in the measuring method of the present invention is not particularly limited as long as it is a concentration which enables the measuring method of the present invention, and is usually from 0.1 to 15 mmol/L and preferably from 0.2 to 10 mmol/L.

The specimen in the present invention is not particularly limited as long as it is a specimen which enables the measuring method of the present invention. Examples thereof include a whole blood, a plasma, and a serum, and are preferred a plasma and a serum.

The component to be measured in the present invention is not particularly limited as long as it is a component to be measured which is converted into hydrogen peroxide and is determined by measuring the hydrogen peroxide. Examples thereof include substrates such as total cholesterol (TC), cholesterol in high-density-lipoprotein (HDL-C), cholesterol in low-density lipoprotein (LDL-C), cholesterol in very-low-density lipoprotein (VLDL-C), cholesterol in remnant-like lipoprotein (RLP-C), glucose, uric acid, triglycerides (TG), phospholipids, choline, creatine, creatinine, lactic acid, and pyruvic acid, as well as enzymes such as cholinesterase and guanase.

In the present invention, a component to be measured is converted to hydrogen peroxide through an enzymatic reaction. Examples of the combination of a component to be measured and a component to convert the component to be measured to hydrogen peroxide through an enzymatic reaction include the following combinations:

TC, HDL-C, LDL-C, VLDL-C, RLP-C: cholesterol esterase and cholesterol oxidase
Glucose: glucose oxidase
Uric acid: uricase
TG: lipoprotein lipase, glycerol kinase, and glycerol-3-phosphate oxidase
Phospholipid: phospholipase D and choline oxidase
Choline: choline oxidase
Creatine: creatinase and sarcosine oxidase
Creatinine: creatininase, creatinase, and sarcosine oxidase
Lactic acid: lactic acid oxidase
Pyruvic acid: pyruvic acid oxidase
Cholinesterase: 2,4-dimethoxybenzoyl choline and choline oxidase
Guanase: guanine, xanthine oxidase, and uricase The peroxidase in the present invention is not particularly limited as long as it is a peroxidase which enables the measuring method of the present invention. Examples thereof include a peroxidase derived from an animal, a plant, or a microorganism, as well as a peroxidase produced by genetic engineering techniques. The concentration of the peroxidase in the measuring method of the present invention is usually from 1 to 100 kU/L.

The oxidative-coloring chromogen in the present invention is not particularly limited as long as it is an oxidative-coloring chromogen which enables the measuring method of the present invention. Examples thereof include a leuco chromogen and an oxidative-coupling coloring chromogen. A leuco chromogen is a substance which is converted in itself to a dye in the presence of hydrogen peroxide and a peroxidase, and examples thereof include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 10-N-(carboxymethylaminocarbonyl)-3,7-bis(dimethylamino)-10H-phenothiazine sodium salt (DA-67), 4,4'-bis(dimethylamino)diphenylamine, and bis[3-bis(4-chlorophenyl)methyl-4-dimethylaminophenyl]amine (BCMA).

An oxidative-coupling coloring chromogen is a substance in which two compounds are oxidatively coupled in the presence of hydrogen peroxide and a peroxidase to thereby form a dye. Examples of the combination of two compounds include a combination of a coupler and an aniline and a combination of a coupler and a phenol.

Examples of the coupler include 4-aminoantipyrin (4-AA) and 3-methyl-2-benzothiazolinone hydrazone.

Examples of the aniline include N-(3-sulfopropyl) aniline, N-ethyl-N-(2-hydroxy-3-sulfopropyl)-3-methylaniline (TOGS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3- methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS).

Examples of the phenol include phenol, 4-chlorophenol, 3-methylphenol, and 3-hydroxy-2,4,6-triiodobenzoic acid (HTIB).

The concentration of the oxidative-coloring chromogen in the measuring method of the present invention is not particularly limited as long as it is suitable for measuring of hydrogen peroxide, and the concentration is usually from 0.01 to 10 g/L.

Measurement of a component to be measured in the present invention is carried out usually in an aqueous medium having a pH of 4.0 to 10.0 and preferably in an aqueous medium having a pH of 6.0 to 8.0. Examples of the aqueous medium include a deionized water, a distilled water, and a buffer solution, and is preferred a buffer solution. Examples of the buffer solution include a phosphate buffer solution, a citrate buffer solution, a borate buffer solution, a carbonate buffer solution, and a Good's buffer solution. Examples of the buffer used in Good's buffer solution include 2-morpholinoethanesulfonic acid (MES), tris(hydroxymethyl)aminomethane (Tris), bis (2-hydroxyethyl) iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), piperazine-N,N'-bis(2-hydroxypropanesulfonic acid) (POPSO), N-[tris(hydroxymethyl)methyl]glycine (Tricine), N,N-bis(2-hydroxyethyl)glycine (Bicine), N-tris(hydroxymethyl) methyl-3-aminopropanesulfonic acid (TAPS), N-cyclohexyl-2-aminoethanesulfonic acid (CHES), and N-cyclohexyl-3-aminopropanesulfonic acid (CAPS).

In addition, a surfactant, a preservative and the like may coexist in the measuring method of the present invention. Examples of the surfactant include a nonionic surfactant, a cationic surfactants, an anionic surfactant, and an amphoteric surfactant. Examples of the preservative include an azide, a chelator, and BioAce. Examples of the azide include sodium azide. Examples of the chelator include ethylenediaminetetraacetic acid (EDTA) and a salt thereof. Examples of the salt include a sodium salt and a potassium salt. In addition to these, a ferrocyanide and a protein such as bovine serum albumin (BSA), which are known as an agents to suppress the influence of bilirubin, may be allowed to coexist.

The measuring reagent of a component to be measured in a specimen of the present invention is a reagent used in the measuring method of the present invention and comprises a component for converting the component to be measured to hydrogen peroxide through an enzyme reaction, a peroxidase, an oxidative-coloring chromogen, and a fatty acid or a salt thereof. Examples of the component for converting the component to be measured to hydrogen peroxide through an enzyme reaction, the peroxidase, the oxidative-coloring chromogen, and the fatty acid or the salt thereof include the component for converting the component to be measured to hydrogen peroxide through an enzyme reaction, the peroxidase, the oxidative-coloring chromogen, and the fatty acid or the salt thereof mentioned above, respectively.

The measuring reagent of the present invention may be in a freeze dried state or a liquid state. In the case of a reagent in a freeze dried state, the reagent can be dissolved in an aqueous medium to apply for measuring. Examples of the aqueous medium include the aqueous medium mentioned above. In addition, the measuring reagent of the present invention may be in a kit form. Examples of the kit include a two-reagent system kit and a three-reagent system kit.

In the measuring reagent of the present invention, the fatty acid is not particularly limited as long as it is contained in a content that provides a concentration which enables the measuring method of the present invention. The fatty acid is contained in a content that provides a concentration of usually 0.1 to 60 mmol/L and preferably 0.2 to 40 mmol/L in a state of being dissolved in an aqueous medium.

In the measuring reagent of the present invention, the peroxidase is not particularly limited as long as it is contained in a content that provides a concentration which enables the measuring method of the present invention. The peroxidase is contained in a content that provides a concentration of usually 0.01 to 40 g/L in a state of being dissolved in an aqueous medium.

In the measuring reagent of the present invention, the oxidative-coloring chromogen is not particularly limited as long as it is contained in a content that provides a concentration which enables the measuring method of the present invention. The oxidative-coloring chromogen is contained in a content that provides a concentration of usually 0.01 to 40 g/L in a state of being dissolved in an aqueous medium.

The measuring reagent of the present invention may comprise the surfactant, preservative and the like mentioned above. In addition to these, a ferrocyanide and a protein such as bovine serum albumin (BSA), which are known as an agent to suppress the influence of bilirubin, may be contained.

Hereinbelow, the invention will be described in more detail with reference to Examples, but these Examples are not intended to limit the scope of the present invention in any way. It is to be noted that reagents and enzymes from the following manufacturers were used in Examples, Comparative Examples, and Test Examples.

MOPS (manufactured by DOJINDO LABORATORIES), sodium acetate trihydrate (manufactured by KANTO CHEMICAL CO., INC.), EMSE (manufactured by Daito Chemix Corporation), 4-AA (manufactured by ACTEC), boric acid (manufactured by Wako Pure Chemical Industries, Ltd.), sodium azide (manufactured by Wako Pure Chemical Industries, Ltd.), NONION HS-210 (manufactured by NOF CORPORATION), EDTA.2Na (manufactured by DOJINDO LABORATORIES), sodium dextran sulfate (molecular weight: 500,000) (manufactured by PK Chemicals), sodium sulfate (manufactured by KANTO CHEMICAL CO., INC.), BSA (manufactured by Millipore), EMULGEN L-40 (manufactured by Kao Corporation), Pluronic L121 (manufactured by ADEKA), potassium ferrocyanide (FCK; manufactured by KANTO CHEMICAL CO., INC.), tetradecyltrimethylammonium chloride (manufactured by Wako Pure Chemical Industries, Ltd.), sodium octanoate (manufactured by Tokyo Chemical Industry Co., Ltd.), sodium decanoate (manufactured by Tokyo Chemical Industry Co., Ltd.), sodium laurate (manufactured by Tokyo Chemical Industry Co., Ltd.), sodium oleate (manufactured by Tokyo Chemical Industry Co., Ltd.), sodium linoleate (manufactured by Tokyo Chemical Industry Co., Ltd.), linolenic acid (manufactured by Tokyo Chemical Industry Co., Ltd.), sodium dodecyl sulfate (SDS; manufactured by Wako Pure Chemical Industries, Ltd.), peroxidase (POD; manufactured by TOYOBO CO., LTD.), ascorbate oxidase (AOD; manufactured by Asahi Kasei Corporation), uricase (manufactured by TOYOBO CO., LTD.), LPL311 (lipoprotein lipase; manufactured by TOYOBO CO., LTD.), and CHO-CE (cholesterol oxidase; manufactured by KIKKOMAN CORPORATION).

EXAMPLES

Example 1

Measuring kits of uric acid (kits A1 to A6) comprising a first reagent and a second reagent below were prepared.

| First reagent | |
|---|---|
| MOPS (pH 7.0) | 20 mmol/L |
| Sodium acetate trihydrate | 15 g/L |
| EMSE | 0.2 g/L |
| Boric acid | 0.1 g/L |
| Sodium azide | 0.2 g/L |
| NONION HS-210 | 1 g/L |
| POD | 5 kU/L |
| AOD | 3 kU/L |
| Fatty acid (see Table 1) | |
| Second reagent | |
| MOPS (pH 7.0) | 20 mmol/L |
| Sodium acetate trihydrate | 12.5 g/L |
| 4-AA | 0.35 g/L |
| EDTA•2Na | 0.5 g/L |
| NONION HS-210 | 0.5 g/L |
| Sodium azide | 0.2 g/L |
| POD | 10 kU/L |
| Uricase | 0.75 kU/L |

Comparative Example 1

A measuring kit of uric acid (kit a1) comprising a first reagent and a second reagent below was prepared.

| First reagent | |
|---|---|
| MOPS (pH 7.0) | 20 mmol/L |
| Sodium acetate trihydrate | 15 g/L |
| EMSE | 0.2 g/L |
| Boric acid | 0.1 g/L |
| Sodium azide | 0.2 g/L |
| NONION HS-210 | 1 g/L |
| POD | 5 kU/L |
| AOD | 3 kU/L |
| Second reagent | |
| MOPS (pH 7.0) | 20 mmol/L |
| Sodium acetate trihydrate | 12.5 g/L |
| 4-AA | 0.35 g/L |
| EDTA•2Na | 0.5 g/L |
| NONION HS-210 | 0.5 g/L |
| Sodium azide | 0.2 g/L |
| POD | 10 kU/L |
| Uricase | 0.75 kU/L |

Comparative Example 2

A measuring kit of uric acid (kit a2) comprising a first reagent and a second reagent below was prepared.

| First reagent | |
|---|---|
| MOPS (pH 7.0) | 20 mmol/L |
| Sodium acetate trihydrate | 15 g/L |
| EMSE | 0.2 g/L |
| Boric acid | 0.1 g/L |
| Sodium azide | 0.2 g/L |
| NONION HS-210 | 1 g/L |
| POD | 5 kU/L |
| AOD | 3 kU/L |
| SDS | 1 mmol/L |
| Second reagent | |
| MOPS (pH 7.0) | 20 mmol/L |
| Sodium acetate trihydrate | 12.5 g/L |
| 4-AA | 0.35 g/L |
| EDTA•2Na | 0.5 g/L |
| NONION HS-210 | 0.5 g/L |
| Sodium azide | 0.2 g/L |
| POD | 10 kU/L |
| Uricase | 0.75 kU/L |

Example 2

Uric acid in a specimen was measured using the kit A1 of Example 1 according to the following procedure.

(1) Preparation of a Calibration Curve

The following reaction was carried out on a Hitachi 7170S automatic analyzer using both of saline (uric acid concentration: 0 mg/dL) and Liquid control serum Wako II (uric acid concentration: 9.4 mg/dL; manufactured by Wako Pure Chemical Industries, Ltd.) as a standard solution and the kit A1 of Example 1. A calibration curve representing a relation between the uric acid concentration and the "absorbance" (the value obtained by subtracting E1 from E2) was prepared based on two absorbances (E1 and E2) obtained from the reaction.

The standard solution (3.1 µL) and the first reagent (0.15 mL) were added to a reaction cell and incubated at 37° C. for 5 minutes. The absorbance (E1) of the reaction solution was measured at a main wavelength of 600 nm and a sub-wavelength of 700 nm. Subsequently, the second reagent (0.05 mL) was added to this reaction solution and further incubated at 37° C. for 5 minutes. The absorbance (E2) of the reaction solution was measured at a main wavelength of 600 nm and a sub-wavelength of 700 nm.

(2) Preparation of a Specimen for Measurement

To 220 µL of biochemical control serum "QAP trot 2×" (manufactured by Sysmex Corporation), 30 µL of Interference check A Plus-bilirubin C having a bilirubin concentration of 500 mg/dL (manufactured by Sysmex Corporation) was mixed to prepare a bilirubin-containing specimen having a bilirubin concentration of 60 mg/dL. Similarly, a control specimen having a bilirubin concentration of 0 mg/dL was prepared using Interference check A Plus-bilirubin C (blank) (manufactured by Sysmex Corporation) instead of Interference check A Plus-bilirubin C having a bilirubin concentration of 500 mg/dL.

(3) Measurement of the "Absorbance" for the Specimen by Reaction of the Specimen with Each of the Kits of Example 1

The "absorbance" for the specimen was measured by the same method as the method for calculating the "absorbance" in (1), except that each of the specimens for measurement prepared in (2) above, that is, the bilirubin-containing specimens and the control specimen was used instead of the standard solution used in preparation of a calibration curve of (1) above.

(4) Determination of the Concentration of Uric Acid in the Specimen for Measurement The concentration of uric acid in each of the specimens was determined from the "absorbances" measured in (3) above and the calibration curve prepared in (1) above. The relative values of the concentrations of uric acid in the bilirubin-containing specimens, when the concentration of uric acid in the control specimen being defined as 100, are shown in Table 1.

The relative value of the concentration of uric acid in the bilirubin-containing specimen was determined by the same method as in (1) to (4) above, except that each of the kits A2 to A6 was used instead of the kit A1. The results are shown in Table 1.

Comparative Example 3

The relative value of the concentration of uric acid in the bilirubin-containing specimen was determined by the same method as in Example 2, except that the kit a1 of Comparative Example 1 was used instead of the kit A1 of Example 2. The results are shown in Table 1.

Comparative Example 4

The relative value of the concentration of uric acid in the bilirubin-containing specimen was determined by the same as in Example 2, except that the kit a2 of Comparative Example 2 was used instead of the kit A1 of Example 2. The results are shown in Table 1.

TABLE 1

| Kit | Fatty acid or SDS (concentration) | Uric acid concentration (relative value) | ΔRelative value |
|---|---|---|---|
| a1 | — | 42.1 | — |
| A1 | Sodium octanoate (10 mmol/L) | 54.4 | +12.3 |
| A2 | Sodium decanoate (1.5 mmol/L) | 54.8 | +12.7 |
| A3 | Sodium laurate (1.0 mmol/L) | 54.5 | +12.4 |
| A4 | Sodium oleate (1.0 mmol/L) | 55.4 | +13.3 |
| A5 | Sodium linoleate (1.0 mmol/L) | 48.3 | +6.2 |
| A6 | Linolenic acid (1.0 mmol/L) | 56.1 | +14.0 |
| a2 | SDS (1.0 mmol/L) | 32.3 | −9.8 |

The relative value of the concentration of uric acid represents a concentration of uric acid in the bilirubin-containing specimen when the concentration of uric acid in the control specimen was defined as 100. The lower the value is, the larger the influence of bilirubin is. Based on the relative value of the concentration of uric acid when the kit a was used, the difference in the relative values of the concentration of uric acid using each of the kits is shown as the Δ Relative value in Table 1. As apparent from Table 1, in the case of using a kit containing SDS having an anionic group like a fatty acid, instead of the fatty acid, the influence of bilirubin was larger than in the case of using a kit containing neither SDS nor fatty acid. In contrast, in the case of using a kit containing a fatty acid but SDS, the influence of bilirubin was smaller than in the case of using a kit containing neither SDS nor fatty acid. This result reveals that the measuring method of the present invention in which fatty acid is used is a method in which the influence of bilirubin is suppressed.

Example 3

Measuring kits of LDL-C (kits B1 to B3) comprising a first reagent and a second reagent below were prepared.

| First reagent | |
|---|---|
| MOPS (pH 7.0) | 20 mmol/L |
| Sodium dextran sulfate (molecular weight: 500,000) | 0.5 g/L |
| Sodium sulfate | 2 g/L |
| EMSE | 0.3 g/L |
| BSA | 4.5 g/L |
| POD | 10 kU/L |
| Fatty acid (see Table 2) | |
| Second reagent | |
| MOPS (pH 7.0) | 20 mmol/L |
| EMULGEN L40 | 7 g/L |
| Pluronic L121 | 3 g/L |
| Tetradecyltrimethylammonium chloride | 0.06 g/L |
| 4-AA | 0.5 g/L |
| BSA | 4.5 g/L |
| FCK | 0.02 g/L |
| POD | 20 kU/L |
| LPL311 | 1.5 kU/L |
| CHO-CE | 1 kU/L |

Comparative Example 5

A measuring kit of LDL-C (kit b) comprising a first reagent and a second reagent below was prepared.

| First reagent | |
|---|---|
| MOPS (pH7.0) | 20 mmol/L |
| Sodium dextran sulfate | 0.5 g/L |
| Sodium sulfate | 2 g/L |
| EMSE | 0.3 g/L |
| BSA | 4.5 g/L |
| POD | 10 kU/L |
| Second reagent | |
| MOPS (pH 7.0) | 20 mmol/L |
| EMULGEN L40 | 7 g/L |
| Pluronic L121 | 3 g/L |
| Tetradecyltrimethylammonium chloride | 0.06 g/L |
| 4-AA | 0.5 g/L |
| BSA | 4.5 g/L |
| FCK | 0.02 g/L |
| POD | 20 kU/L |
| LPL311 | 1.5 kU/L |
| CHO-CE | 1 kU/L |

Example 4

LDL-C in a specimen was measured using the kit B1 of Example 3 according to the following procedure.
(1) Preparation of a Calibration Curve
The following reaction was carried out on a Hitachi 7170S automatic analyzer using both of saline (LDL-C concentration: 0 mg/dL) and Determiner standard serum for measuring HDL/LDL-C (Kyowa Medex Co., Ltd.) as a standard solution and the kit B1 of Example 3. A calibration curve representing a relation between the LDL-C concentration and the "absorbance" (the value obtained by subtracting E1 from E2) was prepared based on two absorbances (E1 and E2) obtained from the reaction.

The standard solution (3.0 μL) and the first reagent (0.15 mL) were added to a reaction cell and incubated at 37° C. for 5 minutes. The absorbance (E1) of the reaction solution was measured at a main wavelength of 600 nm and a sub-wavelength of 700 nm. Subsequently, the second reagent (0.05 mL) was added to this reaction solution and further incubated at 37° C. for 5 minutes. The absorbance (E2) of the reaction solution was measured at a main wavelength of 600 nm and a sub-wavelength of 700 nm.

(2) Preparation of a Specimen for Measurement

To 352 μL of the pooled serum, 48 μL of Interference check A Plus-bilirubin C having a bilirubin concentration of 500 mg/dL (manufactured by Sysmex Corporation) was mixed to prepare a bilirubin-containing specimen having a bilirubin concentration of 60 mg/dL. Similarly, a control specimen having a bilirubin concentration of 0 mg/dL was prepared using Interference check A Plus-bilirubin C (blank) (manufactured by Sysmex Corporation) instead of Interference check A Plus-bilirubin C having a bilirubin concentration of 500 mg/dL.

(3) Measurement of the "Absorbance" for the Specimen by Reaction of the Specimen with Each of the Kits of Example 1

The "absorbance" for the specimen was measured by the same method as the method for calculating the "absorbance" in (1), except that each of the specimens for measurement prepared in (2) above, that is, the bilirubin-containing specimens and the control specimen was used instead of the standard solution used in preparation of a calibration curve of (1) above.

(4) Determination of the Concentration of LDL-C in the Specimen for Measurement

The concentration of LDL-C in each of the specimens was determined from the "absorbances" measured in (3) above and the calibration curve prepared in (1) above. The relative values of the concentrations of LDL-C in the bilirubin-containing specimens, when the concentration of LDL-C in the control specimen being defined as 100, are shown in Table 2.

The relative value of the concentration of LDL-C in the bilirubin-containing specimen was determined by the same method as in (1) to (4) above, except that each of the kits B2 and B3 was used instead of the kit B1. The results are shown in Table 2.

Comparative Example 6

The relative value of the concentration of LDL-C in the bilirubin-containing specimen was determined by the same method as in Example 4, except that the kit b of Comparative Example 5 was used instead of the kit B1 of Example 3. The results are shown in Table 2.

TABLE 2

| Kit | Fatty acid (concentration) | LDL-C concentration (relative value) | ΔRelative value |
|---|---|---|---|
| b | — | 88.3 | — |
| B1 | Sodium laurate (0.2 mmol/L) | 92.9 | +4.6 |
| B2 | Sodium oleate | 91.6 | +3.3 |
| B3 | (0.2 mmol/L) Sodium linoleate (0.2 mmol/L) | 92.0 | +3.7 |

The relative value of the concentration of LDL-C represents a concentration of LDL-C in the bilirubin-containing specimen when the concentration of LDL-C in the control specimen was defined as 100. The lower the value is, the larger the influence of bilirubin is. Based on the relative value of the concentration of LDL-C when the kit b was used, the difference in the relative values of the concentration of LDL-C using each of the kits is shown as the L Relative value in Table 2. As apparent from Table 2, in case using a kit containing a fatty acid, the influence of bilirubin was smaller than in the case of using a kit containing no fatty acid. This result reveals that the measuring method of the present invention in which a fatty acid is used is a method in which the influence of bilirubin is suppressed.

INDUSTRIAL APPLICABILITY

The present invention provides a measuring method of a component to be measured in a specimen while suppressing an influence of bilirubin and a measuring reagent of a component to be measured in a specimen while suppressing the influence of bilirubin. The measuring method and measuring reagent of the present invention are useful for clinical diagnosis.

The invention claimed is:

1. A measuring method of a component to be measured in a specimen, comprising the steps of:
    adding a fatty acid or a salt thereof to an aqueous solution containing the specimen;
    converting the component to hydrogen peroxide through an enzymatic reaction;
    reacting the formed hydrogen peroxide with an oxidative-coloring chromogen in the presence of a peroxidase; and
    measuring an absorbance of the colored reaction solution to thereby determine the component, wherein
    the component is selected from the group consisting of total cholesterol (TC), cholesterol in high-density-lipoprotein (HDL-C), cholesterol in low-density lipoprotein (LDL-C), cholesterol in very-low-density lipoprotein (VLDL-C), cholesterol in remnant-like lipoprotein (RLP-C), glucose, uric acid, triglycerides (TG), phospholipids, choline, creatine, creatinine, lactic acid, and pyruvic acid, and
    the fatty acid or a salt thereof coexists.

2. The measuring method according to claim 1, wherein the fatty acid is a saturated or unsaturated fatty acid having 8 to 24 carbon atoms.

3. The measuring method according to claim 2, wherein the fatty acid is selected from the group consisting of octanoic acid, decanoic acid, lauric acid, myristic acid, palmitic acid, stearic acid, oleic acid, linoleic acid, linolenic acid, eicosatrienoic acid, arachidonic acid, icosanoic acid, eicosatetraenoic acid, eicosapentaenoic acid, docosanoic acid, docosahexaenoic acid, tetradocosanoic acid, and tetracosapentaenoic acid.

* * * * *